United States Patent
Hunter et al.

(10) Patent No.: US 9,739,752 B2
(45) Date of Patent: Aug. 22, 2017

(54) NON DESTRUCTIVE TESTING APPARATUS AND METHOD USING ULTRASOUND IMAGING

(75) Inventors: Alan Joseph Hunter, Delft (NL); Arno Willem Frederik Volker, Delft (NL)

(73) Assignee: NEDERLANDSE ORGANISTIE VOOR TOEGEPAST-NATUURWETENSCHAPPELIJK ONDERZOEK TNO, Delft (NL)

( * ) Notice: Subject to any disclaimer, the term of this patent is extended or adjusted under 35 U.S.C. 154(b) by 406 days.

(21) Appl. No.: 14/130,350

(22) PCT Filed: Jun. 29, 2012

(86) PCT No.: PCT/NL2012/050465
§ 371 (c)(1),
(2), (4) Date: Feb. 7, 2014

(87) PCT Pub. No.: WO2013/006046
PCT Pub. Date: Jan. 10, 2013

(65) Prior Publication Data
US 2014/0140167 A1 May 22, 2014

(30) Foreign Application Priority Data

Jul. 1, 2011 (EP) .................................... 11075155

(51) Int. Cl.
| | |
|---|---|
| *G01N 29/07* | (2006.01) |
| *G01N 29/06* | (2006.01) |
| *G01S 7/52* | (2006.01) |
| *G01S 15/89* | (2006.01) |

(52) U.S. Cl.
CPC ........... *G01N 29/07* (2013.01); *G01N 29/069* (2013.01); *G01S 7/52049* (2013.01);
(Continued)

(58) Field of Classification Search
CPC ................. G01N 29/069; G01N 29/07; G01N 2291/044; G01S 15/8915; G01S 7/52049; G01S 15/8952
(Continued)

(56) References Cited

U.S. PATENT DOCUMENTS 4,744,250 A * 5/1988 Ganglbauer ....... G01N 29/0645
73/588
4,989,143 A * 1/1991 O'Donnell ............. G01H 17/00
600/437

(Continued)

OTHER PUBLICATIONS

A.J. Berkhout, Pushing the limits of seismic imaging, Part I: Prestack migration in terms of double dynamic focusing, Geophysics, vol. 62, No. 3, (1997).
(Continued)

*Primary Examiner* — Paul West
*Assistant Examiner* — Xin Zhong
(74) *Attorney, Agent, or Firm* — Hoffmann & Baron, LLP

(57) ABSTRACT

Improved imaging is provided for structures under test that have propagation direction dependent ultrasound propagation speed or position dependent ultrasound propagation speed due to fibrous, coarse grain or single crystalline material. A set reflection points is selected in the structure under test and ultrasound propagation time delays between the reflection point or points on one hand and the plurality of positions on the other hand that fit an observed time delay of the detected reflections are computed. This may be done by means of an iterative method. In the iterative method a synthetically focused ultrasound beam is realized by summing measurements after compensation for propagation time delay from different transmitting transducers to the reflection points. Time delays to receiving transducers are measured from the arrival time of reflections of this synthetically focused ultrasound beam, and the propagation time delay from different transmitting transducers is iteratively adapted until it matches time delays corresponding to
(Continued)

the measured arrival times. Time delays to other points in the structure under test are interpolated between the selected reflection points and used in the computation of an image of reflections within the structure under test.

14 Claims, 5 Drawing Sheets

(52) U.S. Cl.
CPC .... G01S 15/8915 (2013.01); *G01N 2291/044* (2013.01); *G01S 15/8952* (2013.01)

(58) Field of Classification Search
USPC .................................................. 73/597, 627
See application file for complete search history.

(56) References Cited

U.S. PATENT DOCUMENTS

| 5,388,461 | A | * | 2/1995 | Rigby | ................ | G01S 7/52023 |
| | | | | | | 600/442 |
| 5,423,318 | A | * | 6/1995 | Li | ................ | G01S 15/8906 |
| | | | | | | 600/447 |
| 6,655,213 | B1 | * | 12/2003 | Reinhardt | ................ | G01N 29/07 |
| | | | | | | 73/597 |
| 7,740,583 | B2 | * | 6/2010 | Rigby | ................ | G01S 7/52025 |
| | | | | | | 600/437 |
| 8,707,787 | B1 | * | 4/2014 | Sohn | ................ | G01N 29/4418 |
| | | | | | | 73/597 |
| 2005/0139006 | A1 | * | 6/2005 | Lorraine | ................ | G01N 29/043 |
| | | | | | | 73/597 |
| 2012/0157851 | A1 | * | 6/2012 | Zwirn | ................ | A61B 8/4488 |
| | | | | | | 600/447 |

OTHER PUBLICATIONS

Wilcox et al., Defect characterization using ultrasonic arrays, Proc. of SPIE, vol. 6935, 1, (2008).
Zahiri-Azar R. et al., Time-delay estimation in ultrasound echo signals using individual sample tracking, IEEE Transactions on Ultrasonics, vol. 55, No. 12, (2008).

* cited by examiner

Fig.5a
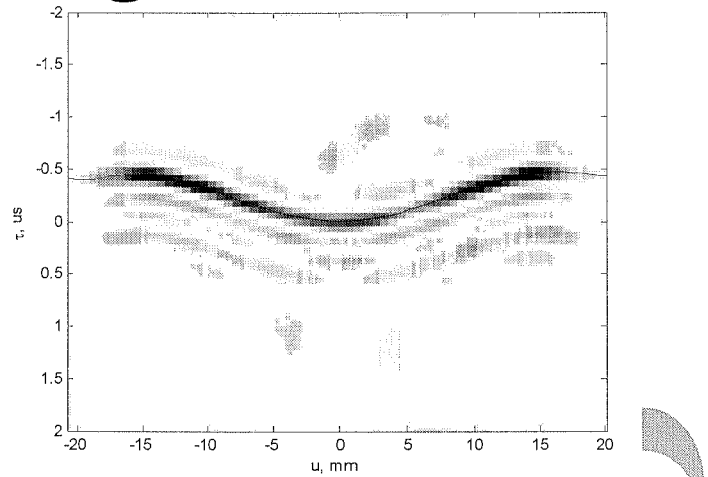
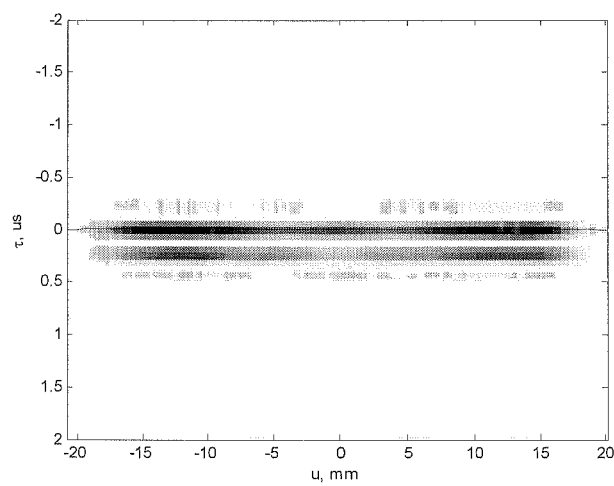
Fig. 5b

NON DESTRUCTIVE TESTING APPARATUS AND METHOD USING ULTRASOUND IMAGING

This application is the U.S. National Phase of, and Applicants claim priority from, International Patent Application Number PCT/NL2012/050465 filed 29 Jun. 2012, which claims priority from EP 11075155.9 filed 1 Jul. 2011, each of which is incorporated herein by reference.

FIELD OF THE INVENTION

The invention relates to a non destructive testing apparatus and method using ultrasound imaging. More in particular, the invention concerns non destructive testing of structures made from anisotropic and/or inhomogeneous coarse grained or fibrous materials using ultrasound imaging.

BACKGROUND ART

It is known to perform non-destructive testing by computing images of the material within a structure from ultrasound reflections within the structure, for example to determine the location of defects like cracks, holes etc. This involves measuring reflected signals, obtained with respective combinations of transmitter and receiver positions. These measurements are processed to obtain image values for different positions in the structure. A known algorithm to compute the image value for an imaged position involves computing synthetic reflection measurements of a synthetic focused transmission directed at the imaged position, by summing measured reflected signals obtained using different transmitter positions multiplied by phase factors that compensate for the differences in phase delay from the transmitter positions to the image position and difference in phase delay from the image position to the receiver positions.

FIG. 1 shows the resulting synthetic signals as a function of receiver position (horizontal) and time between transmission and reception (vertical, time increasing downward) for a simulated structure. Amplitude reflections occur along curves. Each curve corresponds to a reflection point, and in the curve the points correspond to the different travel times to the different reception positions. In the figure the top corresponds to the surface of the structure under test closest to the transducers and halfway a straight line corresponding to the back surface can be distinguished. In between hyperbolic curves for different reflecting points can be a seen. The image intensity for the imaged position is a sum of synthetic signal values along the curve.

This imaging method requires a selection of the phase factors to be used for different imaged positions and the shape of the curve of each imaged position. Assuming constant ultrasound propagation speed throughout the structure, the phase factors and the curves can be computed using geometrical considerations.

However, this method does not give reliable results in structures that comprise anisotropic and/or inhomogeneous materials, such as coarse grained or fibrous materials. In welds, for example, part of the material may have crystallized and other parts may be amorphous, which results in unreliable imaging. Similarly, in material made of fibers in a matrix of resin, the results may be unreliable.

FIG. 2 shows an ultrasound image obtained for an exemplary simulated structure of such a material wherein three point reflectors are present (indicated by circles). Instead of the points, stars are visible. The inventors have found that the unreliability of results of the known method for coarse grained or fibrous materials is at least partly due to anisotropy in the ultrasound propagation speed that results from the presence of grains or fibers. The structure contains three isolated reflectors, but in the image the reflectors are smeared due to the effect of anisotropy.

SUMMARY

It is an object to provide for a non-destructive testing method that uses ultrasound imaging and is capable of producing more reliable images of structures comprising anisotropic and inhomogeneous materials.

A non-destructive testing method is provided, the method comprising transmitting ultrasound signals from a plurality of positions to a structure under test;

detecting, at said plurality of positions, reflections of the transmitted signals from the structure;

selecting a set of one or more reflection points in the structure;

computing ultrasound propagation time delays between the reflection point or points on one hand and the plurality of positions on the other hand that fit an observed time delay of the detected reflections;

using the ultrasound propagation time delays computed for the reflection points to estimate further ultrasound propagation time delays between the plurality of positions and further points in the structure;

computing an image of reflections at said further points from the detected reflections using the estimated ultrasound propagation time delays.

In this way is it is made possible to avoid the effect of anisotropy on image formation. The effects are avoided by using, for each imaged point, a set of ultrasound propagation time delay values to each of the transducers. In an embodiment, imaging may comprise a sum over reflections obtained with respective pairs of transmitting and receiving transducers, with timing offsets to compensate for the ultrasound propagation time delay values between the imaged point and the positions in the pair. Thus, the effect of reflection of ultrasound that interferes coherently at the imaged point is determined. The ultrasound transducers may be located at positions in a one or two dimensional array for example. If a one dimensional array is used, it may be moved along the structure under test, e.g. a pipeline or a plate in a direction transverse to the array.

The sets of set of ultrasound propagation time delay values for the imaged points are determined from a selected set of reflection points in the structure ("in" not excluding reflection points at its surface). Interpolation may be used for the determination for example, which may comprise determining parameters of a model for ultrasound propagation speed that represents speeds dependent on the direction of propagation. Preferably, reflection points are used that exhibit stronger reflections than the average reflection in the structure. In a further embodiment angular filtering may be used to enable selection of different, spatially separate reflection points.

In an embodiment, use is made of the fact that the ultrasound propagation time delay from transducer to the reflection point equals the ultrasound propagation time delay the other way around. Receiver independent compensation may be performed in successive iterations for example, compensating only for the time delays from the transmitters, so that the ultrasound interferes coherently at the reflection point. The time delay of the resulting reflections at different receiving transducers may be compared to the assumed time delays for transmission from these transducers and the assumed time delays may be iteratively adapted until they match. From the field of seismic imaging a related technique is known (A. J. Berkhout, "Pushing the limits of seismic imaging, part 1: prestack migration in terms of double dynamic focusing", Geophysics, VOL. 62, NO. 3 (MAY-JUNE 1997); P. 954-969).

In an embodiment predictions of reflections from the reflection points may be computed and subtracted from the detected reflections. This makes it possible to use more reflection points that have relatively weak reflections to estimate the ultrasound propagation time delays for imaged points more accurately. For example, when interpolation is used, the distance over which interpolation is performed can be made smaller.

In an embodiment the method is applied to a plate, beam or pipeline for example, made of a layered composite containing fibrous material or single crystal grains for example.

A non-destructive testing system and a computer program product for performing non-destructive testing are also provided.

BRIEF DESCRIPTION OF THE DRAWING

These and other objects and advantageous aspects will become apparent from a description of exemplary embodiments, with reference to the following figures

DETAILED DESCRIPTION OF EXEMPLARY EMBODIMENTS

Figure 3:
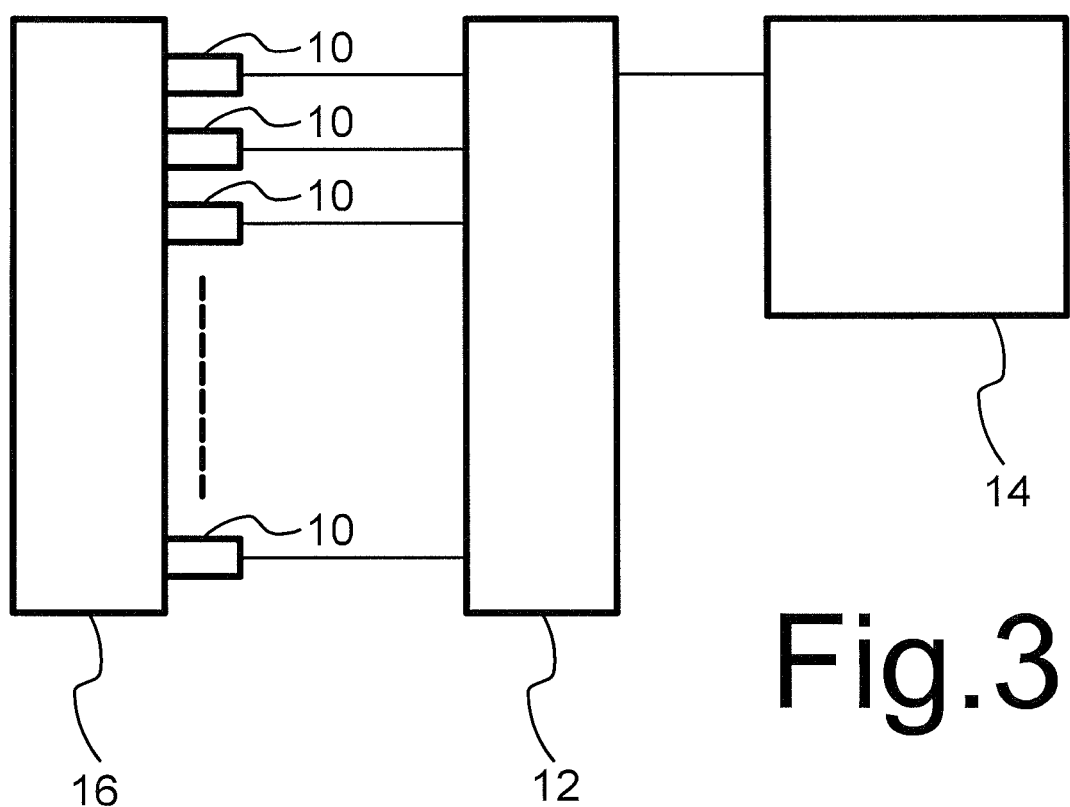
FIG. 3 shows non-destructive testing system

FIG. 3 shows a non destructive testing system comprising an array of ultrasound transducers 10, a processor 12 and an image display device 14. Processor 12 is coupled to ultrasound transducers 10 and image display device 14. Ultrasound transducers 10 are located at different positions on the surface of a structure 16 under test. The structure may be a plate, beam or pipeline for example, made of a layered composite containing fibrous material or single crystal grains for example. In an embodiment ultrasound transducers 10 are arranged in a linear array, for example along a straight line as shown or along a circle segment. In another embodiment a two dimensional array of transducers 10 may be used. When a linear array is used transducers 10 with a planar beam may be used. That is, transducers 10 may be used that emit and receive ultrasound substantially only at zero and small angles (e.g. beam halfwidth at <10 degrees) out of a plane that contains the linear array, but at wider angles within the direction of the plane. In this case the array may be moved along the surface of structure 16 in a direction transverse to the plane to scan the structure.

Figure 4:
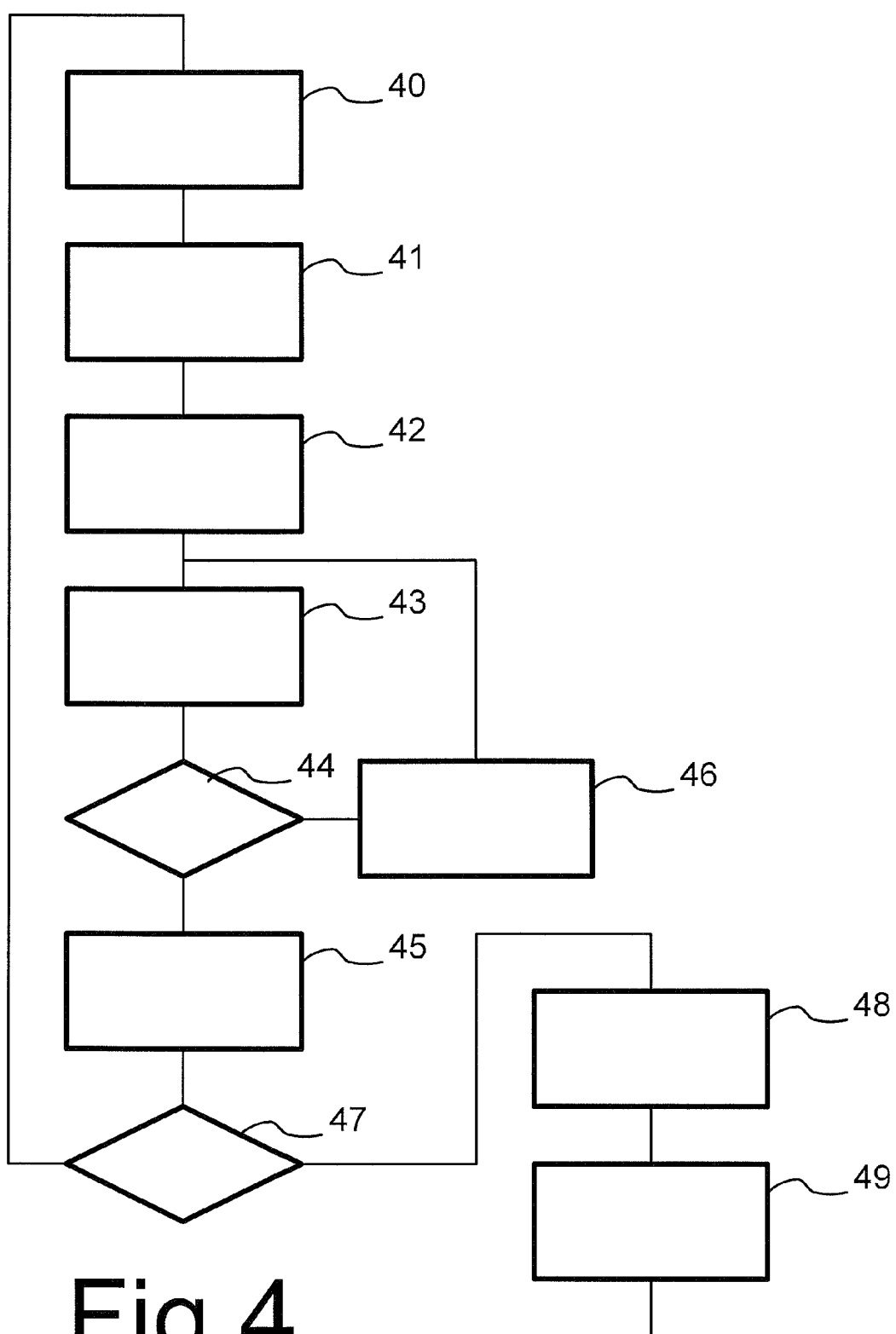
FIG. 4 shows a flow chart of ultrasound image processing FIGS. 5*a, b* show curves of the time of maximum reflection vs position

FIG. 4 shows a flow chart of ultrasound image processing by processor 12. The process will be described using examples for a linear array of transducers 10, but it should be understood that the process can also be applied to a two-dimensional array. At the start of the process, processor 12 is provided with data defining ultrasound propagation speed c in structure 16. Speed values c that are the same for all positions in the structure may be provided for example, but alternatively position r=(x, y), and propagation direction dependent values c(x,y,theta) may be provided (theta representing the direction of propagation in terms of one or more angles).

In a measurement step 40, processor 12 causes respective ones of the transducers 10 in the array to transmit ultrasound signals successively, and processor 12 receives detected ultrasound responses from the transducers 10 in the array for transmissions from each transducer. The process will be described for time dependent functions E(t;n,m), wherein n and m are indices of the transducers 10 with which the ultrasound has been transmitted and received respectively. But it should be understood that an equivalent computation may be performed at least partly in the Fourier transform domain. The time dependent values of the functions E(t;n,m) may be determined by time dependent sampling. Alternatively ultrasound signals with different frequencies may transmitted and received, the time dependent functions E(t; n,m) being determined by means of a Fourier transform.

Figure 1:
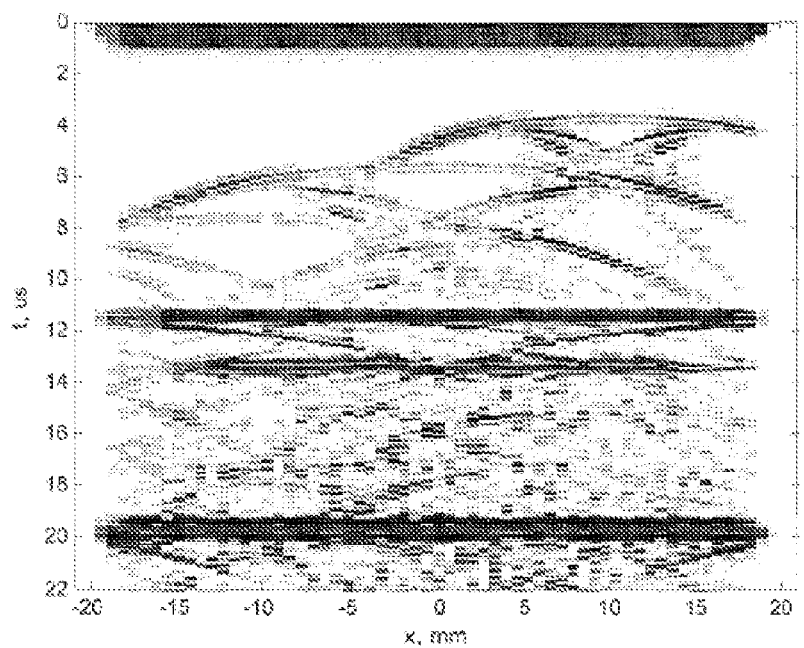
FIG. 1 shows simulated signals of a prior art technique
Figure 2:
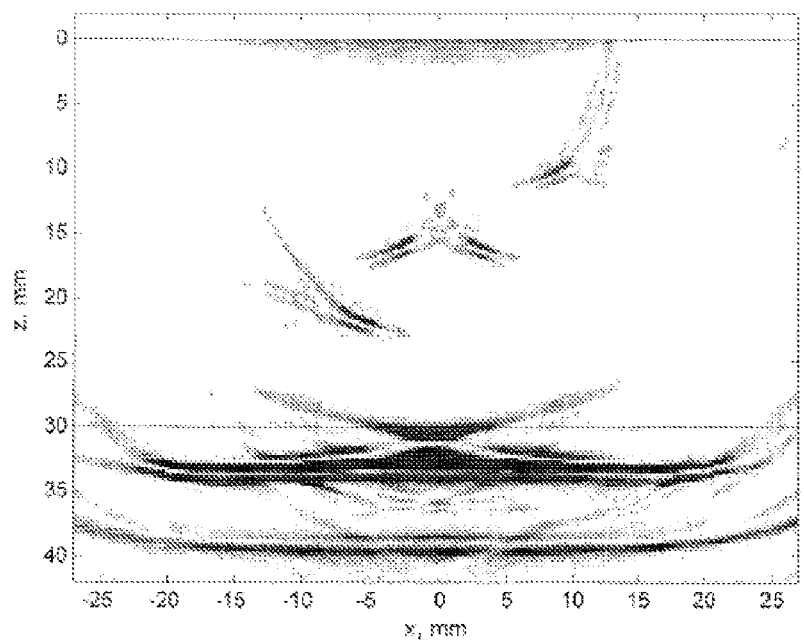
FIG. 2 shows a simulated ultrasound image of a prior art technique

In a first step 41, processor 12 selects an image position R where a reflection occurs. In the example of FIG. 2, the rightmost of the three reflection points may be selected for example. The method of selection is not critical. The reflection point A may be selected based in the measurements E(t;n,m) for example. In an embodiment the selection may comprise detecting, for each transducer n the time delay to a maximum amplitude E(t;n,n) in the signal response to transmission from the transducer and selecting the transducer with index "No" that receives the earliest reflection. The selected position R may be set to the position of this transducer No, offset in a direction perpendicular to a line or plane of the array by a distance equal to half the time delay between transmission and reflection from the point at this transducer, divided by the assumed ultrasound propagation speed. Another approach could be to detect the position of a scatterer/reflector in an approximate image generated using the initial estimate of the propagation speed. If prior knowledge of the position of reflecting objects is available, this could be used to select the position instead. It may be preferred that an isolated reflection point is selected that is not part of a set of mutually similar reflection points at a continuous set of positions. But it has been found that the method also works if an individual reflection point from such a set is selected. An arbitrary reflection point on a line of reflection points or a planar reflecting surface have also been found to provide good results.

In a second step 42, processor 12 computes a set of ultrasound time delay values T(r;R) from the positions r of different one of transmitting transducers 10 to the selected position R, using the assumed ultrasound propagation speed c. When this speed c does not depend on position, the time delay value would be $$T(r;R)=|r-R|/c$$

In a third step 43 processor 12 computes auxiliary synthetic reflection signals for different receiving transducer positions r(m) by computing sums E'(t; r(m)) of measured reflections E(t; n, m) to those receiving transducer positions r(m) from different transmitting transducers positions r(n). In the sum the measured reflections E(t; n, m) are compensated for transmission time delays from the different transmitting transducer positions r(n) to the selected point R. The computation may be performed according to the following formula $$E'(t;r(m))=\text{Sum } E(t-T(r(n);R),n,m)$$

Herein the sum is taken over positions r(n) of transmitting transducers 10 in the array. It may be noted that only the delays T(r(n);R) from the transmitting transducers 10 are used and not the delays T(r(m);R) from the receiving transducers 10.

From the computed auxiliary synthetic reflection signals, remaining time delays from the reflector position R to receiving transducers 10 at different positions r(m) may be estimated, for example by determining the time delay Tmax (r(m)) until a maximum value of the auxiliary synthetic reflection signal E' is reached.

$$T\max(r(m)) = \text{argmax } E'(t;r(m))$$

(herein argmax selects the time value for which the auxiliary synthetic reflection signal E'(t;r(m)) is maximal) This quantity can be compared with the time delays T(r(m);R) provided as input to third step 43, initially by second step 42. If the time delays T(r(m);R) would correspond to the measurements, for each receiving transducer Tmax(r(m)) and T(r(m);R) should be equal.

The detected time delays Tmax define a curve (or surface in the case of a two dimensional array of transducers 10) of time delay as a function of receiving transducer position r(m). FIG. 5*a* E' as grey intensity as a function of transducer position (x-horizontally) and time (converted to vertical position z), wherein T(r;R) according to the time delay values has been subtracted. If the time delays were correct, a intensity concentrated in a straight line would be expected.

In a fourth step 44, processor 12 determines whether iteration is needed. In an embodiment this is done by comparing the time delay values Tmax(r(m)) and T(r(m);R). In an alternative embodiment processor 12 may stop the iterations once a predetermined number of iterations has been performed.

If processor 12 detects in fourth step 44 that the difference between the curves is below a threshold, processor 12 proceeds to a fifth step 45. Any measure of difference between the curves may be used. For example a measure of difference such as the maximum of the differences for all transducer positions may be used, or a sum of the differences or powers of the difference for different transducer positions may be used. This measure of difference may be compared to a predetermined threshold.

If a new iteration is needed, processor 12 executes a sixth step 46, wherein processor 12 determines for each receiving transducer 10 (indexed by m) the difference between the Tmax(r(m)) time delay and the T(r(m);R) time delay for the receiving transducer m (qqq shortest). The difference is multiplied by a factor alpha and added to the time delay values. That is, T(r(m);R) is replaced by $$T(r(m);R) + \text{alpha}*\{T\max(r(m)) - T(r(m);R)\}$$

The factor alpha may be 0.5 for example. Subsequently, the method is repeated from the third step 43, using the updated values of T(r(m);R) instead of the initial values from second step 42.

FIG. 5*b* shows the same data as FIG. 5*a* after ten iterations. As can be seen the intensity is concentrated in straight lines, independent of transductor position. This means that Tmax(r(m)) and T(r(m);R) have converged. After convergence processor 12 executes fifth step 45 wherein processor 12 stores the resulting set of time delay values {T(r(m);R)} for the different transducer positions r(m) and the reflector position R. Furthermore in fifth step 45, processor 12 may determine the amplitude A(t;m,n) of the reflection corresponding to the position R. This amplitude may be determined by applying the delay T(r(n),R) and an amplitude factor f(n) to the auxiliary synthetic reflection signals: A(t;m,n)=f(n)*E'(t+T(r(n),R),m).

The amplitude factor f(n) represents the ratio between the amplitude decrease factor for ultrasound propagation from the transmitting transducer 10 n to the reflection point and a sum of such decrease factors over all transducers 10. This ratio may be determined using the assumption that the amplitude decrease factor for ultrasound propagation from a transmitting transducer 10 to the reflection point equals the amplitude decrease factor for propagation from the reflection point to that transducer 10 when it is used as a receiving transducer. Hence the ratio equals a further ratio of E'(t−T(r(m),R),m) and the sum over m' of E'(t−T(r(m'),R),m') to any time t may be used. This further ratio may be used, or a fitted ratio that best fits the further ratio for a set of time values.

In an embodiment, processor 12 uses the amplitude and the time delays to compute compensated measurements Ec(t;m,n), by subtracting a predicted response due to the reflection at this position from the measurements E(t;m,n):

$$Ec(t;m,n) = E(t;m,n) - A(t;m,n)$$

It should be emphasized that this step is optional: if no reflection points are used that have much weaker reflection than more dominant reflection points, compensated measurements are not needed. Even if reflection points with such weaker reflections are used it may suffice to apply a filter operation to the measurements that attenuates the effect of reflections from a region containing a strong reflector but not reflections from other regions.

In a seventh step 47, processor 12 determines whether the process should be repeated from first step 41 for different reflection positions. In an embodiment processor 12 may do so by computing whether the compensated measurements Ec contain more than a predetermined threshold amount of reflection power. In another embodiment, processor 12 may do so if no further reflection point of more than predetermined strength can be found in first step 41, or if at least a predetermined number of reflection points has been found. If processor 12 determines that the process should be repeated, processor 12 repeats the method from first step 41, using the compensated measurements instead of the current measurements.

When the process is repeated from first step 41, reflection points distributed over a wide spatial range are preferably selected. In an embodiment, regions of positions within a predetermined distance from previously selected reflection points may be excluded from selection. In another embodiment different angular filters may be used in the execution of first step 41 in different repetitions. This may ensure that reflection points separated by a wide spatial range will be selected in different repetitions. An angular filter may be realized for example by computing a sum similar to that used for computing E'(t;r(m)), but wherein the measurements E(t;m,n) are weighted by means of weight factors that decrease towards zero with distance from the region wherein a reflection position is searched for. The decrease of the weight factors is selected to widen the region of locations in the structure under test that will provide significant net contributions to the sum. In the sum any location in the region may be used.

In successive repetitions this fifth step 45 processor 12 produces a plurality of stored sets of time delay values, for respective reflector positions R(k) (k indexing different reflection points), each set comprising time delays T(r(m); R(k)) for each of the transducer positions r(m). If processor 12 determines that no more repetitions are needed, processor 12 executes an eight and ninth step 48, 49 for an array of image positions p(i,j).

In eight step 48, processor 12 computes a respective interpolated set of time delay values Tint(i,j;m) for each image position p(i,j) and for different transducer positions r(m), by interpolation from the stored sets of time delay values. Any interpolation technique may be used. In an embodiment, the interpolation is a sum $$T(i,j;m)=\text{Sum } W(p(i,j),R(k))*T(r(m);R(k))$$

Herein the sum is taken over the reflector positions R(k) (i.e. over k) for which time delays have been determined and the coefficients W are interpolation coefficients, which may satisfy the conditions W(x;x)=1 and sum W(x;R)=1, the sum being taken over R. W(x;R(k)) for any k and x may be taken not less than zero for example. Methods for selecting interpolation coefficients for interpolating between a set of points R(k) are known per se. For example, coefficients may be used that depend linearly on the distance r(m)−R(k) to surrounding reflector positions R(k).

When transducers 10 are used that are sensitive substantially only in a plane (the array being moved in a direction transverse to the plane to obtain measurements in different planes), the interpolation need only interpolate in two dimensions in that plane, and imaging in that plane will be performed. In other embodiments three dimensional interpolation may be used.

In a ninth step 49, processor 12 uses the interpolated set of time delay values Tint(i,j;m) to compute image values I(i,j) for the image positions p(i,j), from the reflection measurements. In one example of such an image computation $$I(i,j)=\text{Sum } E(t-T(i,j;n)-T(i,j;m),n,m)$$

The sum being taken over transmitting and receiving transducers indexed by n and m. However, other image computation techniques for computing an image based on measured ultrasound reflection E using pairs of receiving and transmitting transducers at sets of locations as a function of time are known per se. When these techniques require time delays from transducers to imaged points (explicitly, or implicitly in the form of a distance between transducers to imaged points divided by an assumed speed of sound), these time delays may be replaced by the interpolated time delays T(i,j;m). Processor 12 causes image display device 14 to display the resulting image.

Figure 6:
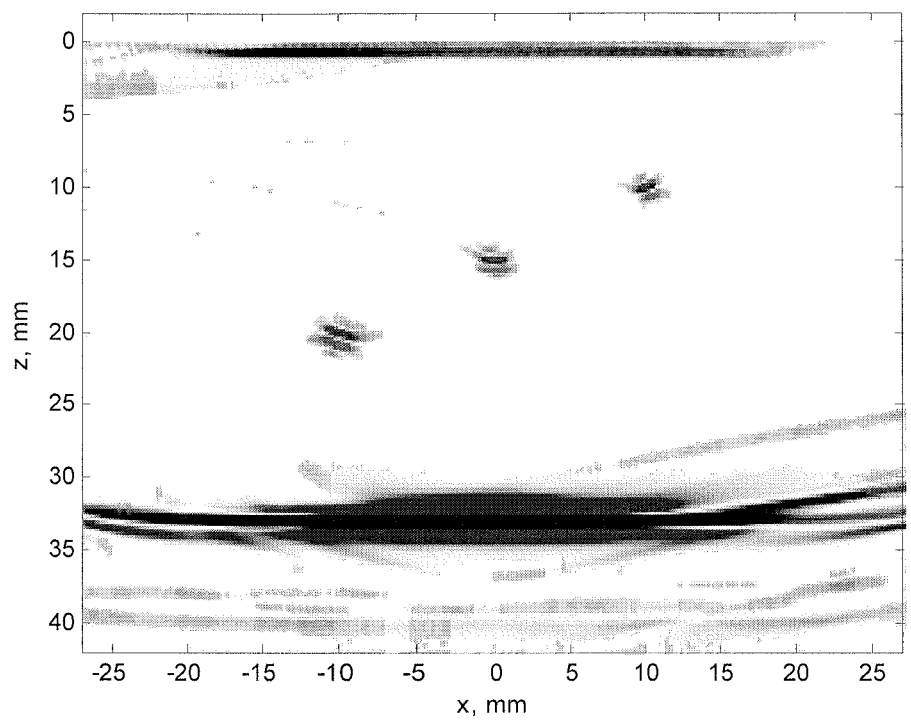
FIG. 6 shows an ultrasound image

FIG. 6 shows an image of a simulated structure that has been obtained in this way. This image should be compared with that of FIG. 2. In the computation of the image of FIG. 2, position dependence of the time delay was not taken into account. This has the effect that for different pairs of transmitting and receiving transducers reflections from the same reflection point appear to come from different locations in the tested structure, which leads to defocusing and/or ghost reflections. In comparison, FIG. 6 shows that such effects can be removed by first computing interpolated time delays T(i,j;m).

This technique makes it possible to compensate for differences between ultrasound propagation speeds in the material between a location in the structure under test and different transducers. Such differences may arise for example if the structure under test comprises crystalline material, wherein the ultrasound propagation speed depends on the direction of the propagation relative to the crystal axes, or a fibrous material, wherein the ultrasound propagation speed depends on the direction of the propagation relative to fiber directions. Inhomogeneity of the structure under test may also lead to differences in the propagation speeds.

The interpolation of the time delay values makes it possible to handle structures under test that contain only a limited number of reflection points, such as single crystals or structures with fibrous material. Preferably, the selection of reflection points is made to include reflection points at the boundary of the structure under test. This provides for a more reliable interpolation of the time delays for image positions in a range towards the boundary. However, even if reflection points on the boundaries, or all boundaries, of the structure under test are not available the method can still be used. The interpolation can be extended beyond the volume between the selected reflection points. Although strictly speaking this can be called extrapolation, the term "interpolation" is used herein to cover such an extension as well. In an alternative embodiment, the computation of the image using the interpolated time delays may be limited to the volume between the selected reflection points.

It is preferred to interpolate using a plurality of reflection points, for example at least two if the time delays are interpolated along a line, at least three if the time delays are interpolated along a plane and at least four if the time delays are interpolated in a three dimensional volume. More reflection points may be used to obtain a more detailed interpolation However, fewer reflection points may suffice if an interpolation model is used. An interpolation model may define position propagation direction dependent ultrasound propagation speeds as a function of one or more parameters. In this case the values of the parameters may be estimated in order to obtain values that follow from the model as interpolated time delay values. In a model for an anisotropic structure, the model may define the speed of propagation for each position in the structure as a function of the direction of propagation at this position. An example of an interpolation model is a model that assumes that ultrasound propagation speeds are the same for all positions obtained by translation along one direction. In this example, the parameters define ultrasound propagation speeds at positions in a plane transverse to that direction. Another example of an interpolation model is a model that assumes that ultrasound propagation speeds are the same for all positions obtained by translation along directions in a plane. In this example, the parameters define ultrasound propagation speeds along a line transverse to that plane. In some cases interpolation models with even less parameters may be needed, for example if the model defines a linear variation of the ultrasound propagation speeds, in which case only the coefficients defining the linear variation are used as parameters. In another example the model may defines a position independent propagation speed that only depends on the direction of propagation of the ultrasound waves. In this case only the ultrasound speeds for different direction of propagation may be used as parameters that will be estimated using the time delays for the reflection points and then applied to determine the time delays for other points in the structure under test.

In the embodiment wherein an interpolation model is used, initial values of the parameters of the model are initially used to set the parameter values of the model. In this embodiment, second step 42 comprises computation of the set of ultrasound time delay values T(r;R) from the positions r of different one of transmitting transducers 10 to the selected position R, using the ultrasound propagation speed defined by the model and the parameter values. When the speed depends on position this may comprise determining ray paths from the transducers to the reflection position R that follow from the model, followed by integrating speeds along the ray paths.

In this embodiment, sixth step 46 may comprise updating the parameters of the model and computation of the set of ultrasound time delay values $T(r;R)$, from the updated model. The update may be performed dependent on the difference $D=T\max(r(m))-T(r(m);R)$. These quantities are a function of the parameters of the model. Methods of updating parameters of a model dependent on a function D that should be made to approach zero are know per se. Instead, sixth step 46 may be left unchanged, the parameters of the model being computed from the time delay values $T(r;R)$. As noted this quantity is a function of the parameters of the model. Inversion methods for computing parameters from such functions are known per se. As noted, it depends on the model how many parameter values need to be determined. When more parameter values need to be determined, correspondingly more reflection points R may be selected. When only a few parameter values are needed, only a few reflection points R, or even only one reflection point R may suffice.

In the embodiment that uses the interpolation model eight step 48 comprises computing a set of time delay values $T\text{int}(i,j;n)$ for each image position $p(i,j)$ and for different transducer positions $r(m)$, based on the interpolation model. Although specific embodiments have been disclosed, it will be appreciated that variations are possible. For example, although the process has been described in terms of specific use of transmitting and receiving transducers, the roles of these transducers in the computation may be interchanged. In this case the auxiliary synthetic reflection signals are computed by compensating for the delays $T(r(n);R)$ between the receivers n and the reflection position R, and the delays between the transmitters and the reflection position R.

Possible implementations of a number of aspects of the described method can be derived from techniques in the field of seismic imaging, such as described by A. J. Berkhout, in "Pushing the limits of seismic imaging, part 1: prestack migration in terms of double dynamic focusing", Geophysics, VOL. 62, NO. 3 (MAY-JUNE 1997); P. 954-969.

Although the use of argmax has been described for determining a time delay Tmax that is compared with $T(r;R)$, it should be appreciated that different methods of determining time delays from the auxiliary synthetic reflection signals may be used, for example by fitting a pulse shape to the auxiliary synthetic reflection signals and using the maximum of the fitted function, taking an average of time values for which the auxiliary synthetic reflection signal has equal heights on mutually opposite sides of a peak etc.

Although a time domain implementation has been described, it should be appreciated that at least part of the computation may be performed in the temporal frequency domain. In this domain time delays T may be represented by corresponding phase factors $\exp(2*i*pi*f*T)$, wherein f is the frequency and of course sums performed with time domain signals can be replaced with sums of frequency domain functions. For the argmax determination a transform to the time domain may be used, but alternatively the argmax of a function may be replaced by a determination of a time delay from a phase shift of the frequency domain version of the reflected signal with respect to the transmitted signal, or a derivative of the phase shift with respect to frequency.

From each transmitting transducer 10 a single transmission of a wide frequency band pulse may be used to measure the resulting reflection signals at the receiving transducers 10. Alternatively, a plurality of narrower band pulses may be transmitted to measure resulting reflection signals at the receiving transducers 10. Instead of transmitting pulses a frequency swept signal may be transmitted to determine reflection as a function of frequency. Signals may be transmitted repeatedly and the resulting repeated reflection signals may be averaged to determine the signals E, or their frequency domain version.

As mentioned, the number of iterations of updates of the time delays $T(r(m);R)$ may be fixed or variable, dependent on convergence. Similarly, the number of reflection point positions R may be fixed or variable and the reflection point positions R may be fixed if they are known in advance.

Although an embodiment has been disclosed wherein the image is formed using only the same the set of measurements from which the time delays have been determined as well, it should be appreciated that instead the time delays determined with one set of measurements may be used as time delays in the image computation using another set of measurements.

Although an embodiment has been disclosed wherein the auxiliary synthetic reflection signals are computed using the same the set of measurements in each iteration, it should be appreciated that alternatively, additional reflection measurements may be performed, for example by simultaneously transmitting ultrasound signals from the transducers at locations $r(m)$ with mutual timing offset according to the delays $T(r(m);R)$. Thus, the transmitted signals will be summed in the structure under test rather than in processor 12. The reflections of these summed signals may be detected and used to determine the time delays as described.

Although an embodiment has been disclosed wherein the image is formed using only the same the set of measurements from which the time delays have been determined as well, it should be appreciated that instead the time delays determined with one set of measurements may be used as time delays in the image computation using another set of measurements.

Although transducers may be used wherein the reception and transmission functions are at least part performed by the same structure, so that the delay times for transmission and reception are identical, it should be appreciated that the reception and transmission function of the transducer may be realized by separate structures, In this case it may be necessary to apply a predetermined correction to the delay times of transmission and reception relative to each other. This need not affect the method, as long as the reception and transmission structures are so close together that the ultrasound paths to and from the structures are so close to each other that the properties of the structure under test do not affect propagation along these paths in substantially different ways.

Processor 12 may be a programmable processor, programmed with a computer program that causes it to execute the described process. The computer program may be provided stored in a computer program product like a computer readable optical or magnetic disk or a semi-conductor memory. Processor 12 may be part of a processing system that comprises no other processors, but alternatively the processing system may comprise a plurality of processors, in which case different parts of the process may be executed by different ones of the processors.

The invention claimed is:

1. A non-destructive testing method, the method comprising:
    transmitting ultrasound signals from a plurality of positions to a structure under test;
    detecting, at said plurality of positions, reflections of the transmitted signals from the structure;

selecting a set of one or more reflection points in the structure;

computing ultrasound propagation travel times for ultrasound travelling along travel paths between the set of one or more reflection points on a first end of each travel path and the plurality of positions on a second end of each travel path by fitting the ultrasound propagation travel times to observed elapsed time delay values between the transmission from the plurality of positions and the detection of the detected reflections at the plurality of positions wherein the computed ultrasound propagation travel times are not equal to the observed elapsed time delay values;

using the ultrasound propagation travel times computed for the set of one or more reflection points to compute estimated further ultrasound propagation travel times for ultrasound travelling between the plurality of positions at first ends of further travel paths and further points in the structure at second ends of further travel paths; and computing an image of reflections at said further points from the detected reflections using the estimated further ultrasound propagation travel times.

2. A method according to claim 1, wherein the set of one or more reflection points comprises a first reflection point, said computing of ultrasound propagation travel times comprising iteratively computing updatable ultrasound propagation travel time values, by determining auxiliary synthetic reflection signals for respective ones of the plurality of positions, by summing detected reflections of ultrasound signals transmitted to or from the respective one of the plurality of positions, from or to the plurality of positions, compensated for the updatable ultrasound propagation travel time values of ultrasound travelling between the first reflection point and the plurality of positions, but not for the updatable ultrasound propagation travel time value between the first reflection point and the respective one of the positions;

determining observed ultrasound propagation travel time values for the respective ones of the plurality of positions from the auxiliary synthetic reflection signals; and updating the updatable ultrasound propagation travel time values dependent on a difference between the updatable ultrasound propagation travel time values and the observed elapsed time delay values.

3. A method according to claim 2, comprising testing whether the difference between the updatable ultrasound propagation travel time values and the observed elapsed time delay values for the plurality of positions meets a predetermined termination criterion and terminating iteration of updating of the updatable ultrasound propagation travel time values when said termination criterion is met.

4. A method according to claim 1 wherein said set of one or more reflection points comprises plurality of reflection points, the reflection points from the set being selected successively, said computing of the ultrasound propagation travel time values between each successive selected reflection point and the plurality of positions comprising computing predicted reflections from a reflection point or points from the set that precedes or precede the successive selected reflection point;

subtracting the predicted reflections from the detected reflections; and computing the ultrasound propagation travel times of ultrasound travelling between the successive selected reflection point and the positions from the plurality of positions that fit the reflection signals from which the predicted reflections have been subtracted.

5. A method according to claim 1, wherein computation of an image value for at least one of the further points comprises summing detected reflections of ultrasound signals transmitted between pairs of positions from the plurality of positions, with a compensation for ultrasound propagation travel time delay of ultrasound travelling between the further points and the positions in the pair, the compensation being based on the estimated further ultrasound propagation travel times.

6. A method according to claim 1, wherein the computation of the estimated further ultrasound propagation travel times of ultrasound traveling between the plurality of positions and at least one of the further points comprises interpolating the ultrasound propagation travel time of ultrasound travelling between the computed ultrasound propagation travel time for a plurality of the reflection points.

7. A method according to claim 1, wherein the ultrasound signals being transmitted through a volume of the structure under test that comprises fibers, grains, and/or single crystal grains.

8. A non-destructive testing system, the system comprising:

a plurality of ultrasound transducers, at respective ones of a plurality of positions; and a processing system coupled to the ultrasound transducers and configured to:

receive detected reflection signals from respective ones of the ultrasound transducers, in response to ultrasound transmission from the transducers;

select a set of one or more reflection points in a structure under test;

compute ultrasound propagation travel times for ultrasound travelling along travel paths between the reflection point or points on a first end of each travel path and the plurality of positions on a second end of each travel path by fitting the ultrasound propagation travel times to observed elapsed time delay values between the transmission from the plurality of positions and the detection of the detected reflections at the plurality of positions, wherein the computed ultrasound propagation travel times are not equal to the observed elapsed time delay values;

use the ultrasound propagation travel times computed for the reflection points in a computation of estimated further ultrasound propagation travel times for ultrasound travelling between the plurality of positions and further points in the structure; and compute an image of reflections at said further points from the detected reflections using the estimated further ultrasound propagation travel times.

9. A system according to claim 8, wherein the processing system is configured to compute the ultrasound propagation travel times iteratively, by:

determining auxiliary synthetic reflection signals for respective ones of the plurality of positions, by summing detected reflections of ultrasound signals transmitted to or from the respective one of the plurality of positions, from or to the plurality of positions, compensated for updatable ultrasound propagation travel time values for ultrasound travelling between the first reflection point and the plurality of positions, but not for the updatable ultrasound propagation travel time value between the first reflection point and the respective one of the positions;

determining observed ultrasound propagation travel time values for the respective ones of the plurality of positions from the auxiliary synthetic reflection signals;

updating the updatable ultrasound propagation travel time values dependent on a difference between the updatable ultrasound propagation travel time values and the observed ultrasound propagation travel time values.

10. A system according to claim 9, comprising testing whether the difference between the updatable ultrasound propagation travel time values and the observed elapsed time delay values for the plurality of positions meets a predetermined termination criterion and terminating iteration of updating of the updatable ultrasound propagation travel time values when said termination criterion is met.

11. A system according to claim 8, wherein said set of one or more reflection points comprises plurality of reflection points, the processing system being configured to select the reflection points from the set successively, said computing of the ultrasound propagation travel time values for ultrasound travelling between each successive selected reflection point and the plurality of positions comprising computing predicted reflections from a reflection point or points from the set that precedes or precede the successive selected reflection point;

subtracting the predicted reflections from the detected reflections;

computing the ultrasound propagation travel times between the successive selected reflection point and the positions from the plurality of positions that fit the reflection signals from which the predicted reflections have been subtracted.

12. A system according to claim 8, wherein computation of an image value for at least one of the further points comprises summing detected reflections of ultrasound signals transmitted between pairs of positions from the plurality of positions, with a compensation for the ultrasound propagation travel time values for ultrasound travelling between the further points and the positions in the pair, the compensation being based on the estimated further travel times.

13. A system according to claim 8, wherein the estimation of the further ultrasound propagation travel time for ultrasound travelling between the plurality of positions and at least one of the further points comprises interpolating the ultrasound propagation travel time for ultrasound travelling between the computed ultrasound propagation travel times for a plurality of the reflection points.

14. A computer program product comprising instructions that, when executed by a programmable processor, will cause the programmable processor to execute the method of claim 1.

\* \* \* \* \*